United States Patent
Ma et al.

(10) Patent No.: US 7,636,549 B2
(45) Date of Patent: Dec. 22, 2009

(54) AUTOMATED BONDING FOR WIRELESS DEVICES

(75) Inventors: Dung T. Ma, Westminster, CA (US); Hao V. Nguyen, Grand Prairie, TX (US)

(73) Assignee: Abbott Medical Optics Inc., Santa Ana, CA (US)

( * ) Notice: Subject to any disclaimer, the term of this patent is extended or adjusted under 35 U.S.C. 154(b) by 557 days.

(21) Appl. No.: 11/408,763

(22) Filed: Apr. 21, 2006

(65) Prior Publication Data
US 2007/0249286 A1   Oct. 25, 2007

(51) Int. Cl.
*H04B 7/00* (2006.01)
*H04M 1/66* (2006.01)
*H04M 1/68* (2006.01)
*H04M 3/16* (2006.01)

(52) U.S. Cl. ........................ 455/41.2; 455/41.3; 455/411
(58) Field of Classification Search ................ 455/41.2, 455/41.3, 411
See application file for complete search history.

(56) References Cited

U.S. PATENT DOCUMENTS

| | | | |
|---|---|---|---|
| 5,433,702 A | * | 7/1995 | Zelman et al. ............... 604/22 |
| 6,880,095 B2 | * | 4/2005 | Cromer et al. .............. 713/300 |
| 7,236,742 B2 | * | 6/2007 | Hall et al. .................. 455/41.3 |
| 2003/0078072 A1 | | 4/2003 | Serceki et al. |
| 2003/0232305 A1 | | 12/2003 | Warner |
| 2004/0115591 A1 | | 6/2004 | Warner |
| 2005/0059354 A1 | * | 3/2005 | Zhao et al. ............... 455/67.11 |
| 2005/0101316 A1 | | 5/2005 | Ido |
| 2005/0130097 A1 | | 6/2005 | Warner |
| 2005/0130098 A1 | | 6/2005 | Warner |
| 2006/0094461 A1 | * | 5/2006 | Hameed et al. .......... 455/552.1 |
| 2006/0219049 A1 | | 10/2006 | Horvath et al. |
| 2009/0174525 A1 | * | 7/2009 | Yamauchi ................... 340/5.8 |

* cited by examiner

Primary Examiner—Matthew D Anderson
Assistant Examiner—Wen W Huang

(57) ABSTRACT

A method and apparatus for managing the establishment of a wireless connection between an instrument host and a non-fixed device is provided. The method comprises acquiring the non-fixed medical device address over a fixed wire by replacing the traditional wireless searching mechanism. The method also comprises providing an authentication mechanism between the instrument host and the non-fixed device, for example, across a wireless communications network.

17 Claims, 8 Drawing Sheets

AUTOMATED BONDING FOR WIRELESS DEVICES

BACKGROUND OF THE INVENTION

1. Field of the Invention

The present invention relates generally to the field of medical systems, and more specifically to managing connection establishment processing for wireless devices.

2. Description of the Related Art

Traditionally, medical system products transmit control signals over a fixed wire or cable using a standard cable interface, such as USB, Ethernet, etc. Current advancements in wireless communications techniques, including short-range radio and light wave technology, enable designers to employ wireless connections to transmit control signals and other data, thus removing the need for a traditional fixed wire or cable. Examples of removable or non-fixed devices include monitors or monitoring equipment, test equipment, remote control devices, and so forth.

The rapid advancement and proliferation of short-range radio technology affords medical system product designers and manufacturers the ability to create and deploy non-fixed subsystems and devices without need for a conventional fixed physical communication cable. For example, non-fixed devices meeting or complying with the Institute of Electrical and Electronics Engineers (IEEE) 802.11g, IEEE 802.15.4 standard (ZigBee), and Ericsson Bluetooth™, referred to herein simply as "Bluetooth," specifications provide short-range radio technology to enable for wireless communications. These technologies allow for wireless transmission of signals over short distances between computers and other electronic devices. Bluetooth enabled devices are capable of an approximate 10-meter transmission range at data rates up to 720 kilobits/sec, and can provide better security features than devices implementing IEEE 802.11g communications.

Although typically not well suited for medical applications, line-of-sight wireless light wave technology, including Infrared Data Association (IrDA) techniques, may also be employed by product designers to realize wireless connections.

Implementing either the Bluetooth or IEEE 802.11g specifications will yield a communications path between wireless non-fixed devices and subsystems. Each specification also addresses providing an interference resistant communications path with automatic error detection and correction capabilities for transmitting and receiving of control signals, data, and information.

In summary, Bluetooth technology enables communication between two wireless devices without use of a fixed cable connection. Bluetooth, ZigBee, and IEEE 802.11g specifications address the establishment of a communications path to form a wireless connection for the transmission and reception of data, control signals and information across a single communications path.

Bluetooth and ZigBee implementations employ a bonding process to establish a new relationship between two Bluetooth enabled devices before they can exchange data. In this context, bonding refers to a mechanism where the two devices are exchanging protected passkeys and form a link. Once bonded, all data and information transmitted over a Bluetooth, ZigBee, or similar link is encrypted and only those slave devices authorized during the bonding process will be able to receive and decipher this encrypted transmission.

In a mass production environment, each slave device of a Bluetooth or similar system requires bonding with a master device in order to perform various quality control tests and safety checks in accordance with Food and Drug Administration and other functional and business requirements. Problems arise in a mass production environment where the potential number of slave devices that may be found available during the searching phase becomes quite large. The searching process associated with master-slave device bonding process may return a long list of addresses in this environment and may easily exceed the search limit defined by the protocol (in the case of Bluetooth, currently 7-9 devices, depending on implementation).

Due to this limitation, the list of addresses may fill up rapidly and thus prevent the desired or intended slave devices from being entered into the list. A manual process of entering the slave device address into the host system in order to bond the devices may replace the searching phase. Today's mass production environments require increasing manual intervention in proportion to factory floor production yield rates to coordinate and manage quality control tests and safety checks. Manual intervention consumes large amounts of time in order to successfully pair all wireless slave devices to a master device and is prone to human errors.

In an operating theater environment, safety issues may arise if the searching process acquires addresses from slave devices already in use. For example, if a non-fixed wireless medical subsystem of device is required to perform a surgical task, it must be first bonded with a instrument host. When the instrument host initiates the bonding process for the non-fixed wireless medical device, the instrument host instructs the master device to search for all slave devices within range. This may become problematic if this search includes slave devices that are within range and currently in-use in an adjacent operating room. Moreover, if the master device successfully bonds with a slave device in a different operating room, not only may this pose a safety hazard, but at a minimum will consumes a great deal of time to eliminate this error. If an enabled slave device requires replacement during an operation, an efficient and reliable bonding process is paramount to continuing the procedure while minimizing disruption.

Mass production environments and surgical operating rooms employing non-fixed wireless medical subsystems and devices require an efficient, accurate and reliable method for searching and pairing a master and slave device to facilitate efficient operation of the mass production line and ensure safety in the operating environment.

Thus it would be advantageous to offer an architecture and design that provide wireless operated subsystems and devices a reliable and accurate connection management scheme to rapidly bond devices.

SUMMARY OF THE INVENTION

According to one aspect of the present design, there is provided a method for establishing a Bluetooth, ZigBee, or similar wireless connection between an instrument host and at least one non-fixed device. The method comprises providing a fixed cable wire connection between the instrument host and the non-fixed device, wherein the instrument host provides master device functionality and the non-fixed device provides slave device functionality, discovering identifying information related to the a slave device (for example a Bluetooth address, or a device identification number or serial number of the non-fixed device), and authenticating the non-fixed device (for example over a wireless communications network).

According to another aspect of the present design, there is provided a connectivity management system, for example, a Bluetooth system. The system comprises an instrument host comprising a bonding utility and a controller configured to control communications with at least one obtain slave device over a fixed wire. The system further comprises a non-fixed device configured to support wired and wireless modes of operation, a fixed wire connecting the instrument host to the non-fixed device, and a wireless communications network. The instrument host is configured to discover identifying information related to the slave device and authenticate the non-fixed device, for example over the wireless communications network.

These and other advantages of the present invention will become apparent to those skilled in the art from the following detailed description of the invention and the accompanying drawings.

BRIEF DESCRIPTION OF THE DRAWINGS

The present invention is illustrated by way of example, and not by way of limitation, in the figures of the accompanying drawings in which.

DETAILED DESCRIPTION OF THE DRAWINGS

Figure 1A:
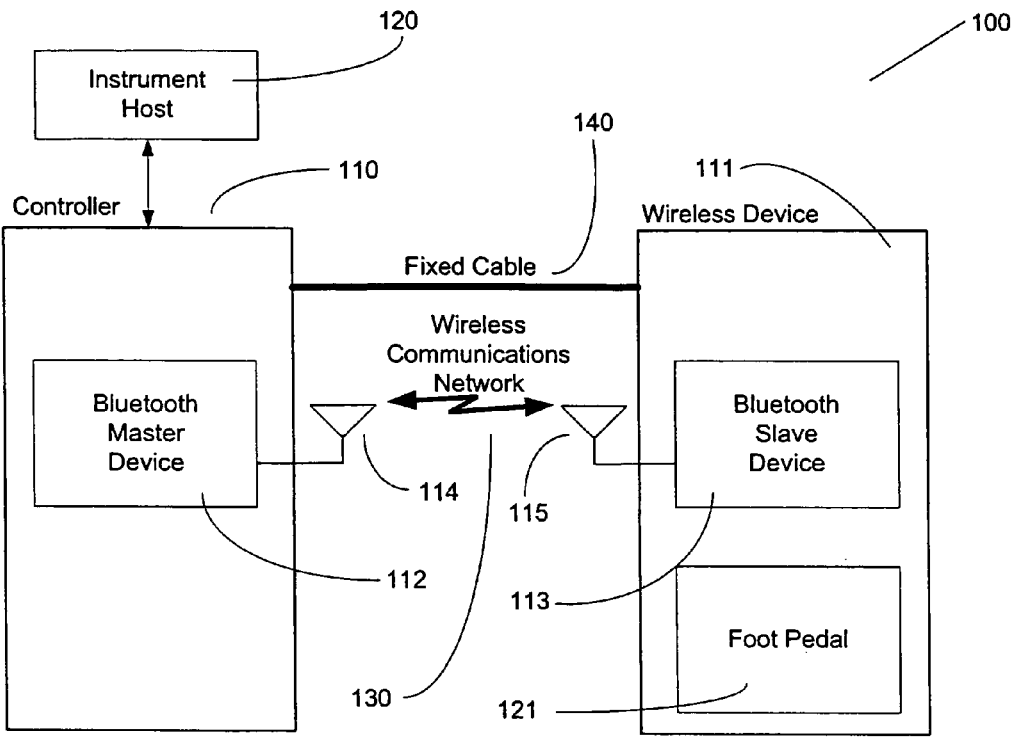
FIG. 1A is a block diagram illustrating the components and interfaces of an exemplary communication system employing Bluetooth wireless communications technology.

The following description and the drawings illustrate specific embodiments sufficiently to enable those skilled in the art to practice the system and method described. Other embodiments may incorporate structural, logical, process and other changes. Examples merely typify possible variations. Individual components and functions are generally optional unless explicitly required, and the sequence of operations may vary. Portions and features of some embodiments may be included in or substituted for those of others.

The present design provides a system and method for managing a connection establishment process within a Bluetooth, ZigBee, or similiar environment. For the purposes of present description, examples will be directed to Bluetooth system. It will be appreciated that embodiments of the invention may be applied to any communication environment in which pairing between devices is used, for example a ZigBee environment. This connection establishment process enables a wireless communications path to be built by bonding a Bluetooth master and slave device for sending and receiving of data across this path.

A connection establishment management arrangement or subsystem may provide a bonding mechanism for establishing a connection between Bluetooth enabled master and slave devices. This arrangement may be suitable for a wireless device or devices that operate in a medical theater, including but not limited to an operating room. The present design may provide an arrangement that enables users of wireless medical devices to rapidly and accurately connect a wireless device. Furthermore, this communications management arrangement or subsystem may also be suitable for a wireless device or devices that require connections to be established in a mass production environment affording rapid and accurate connections.

The communications management subsystem may include a novel wired connection to replace the Bluetooth wireless searching phase. This novel wired connection eliminates any potential human error and reduce the total time required to establish a communications path between a Bluetooth master and slave device.

The present design method is directed to managing an accurate, reliable and efficient means to establish a wireless communications path between Bluetooth enabled master and slave devices, typically employed in a medical scenario but applicable in other scenarios. Communication management may include the discovery of Bluetooth slave device address and may include pairing with the slave device reporting a predetermined Bluetooth address over a wireless network connection with the master device to establish a communications path.

While the present design may be used in various environments and applications, it will be discussed herein with a particular emphasis on a medical or hospital environment, where a surgeon or health care practitioner performs. For example, one embodiment of the present design is a phacoemulsification system or method using a surgical system that incorporates a wireless medical device, such as a wireless footswitch, to control the surgical system.

The term "wireless device" or "wireless medical device" or "non-fixed wireless device" or the like as used herein means a device capable of receiving and/or transmitting information wirelessly, i.e. over the air, using either a radio, light wave (e.g. infrared) or other communication technique that does not require a physical connection, such as a wire. Wireless devices that may realize the reception and transmission of data include, but are not limited to, those devices meeting or complying with the Institute of Electrical and Electronics Engineers (IEEE) 802.11, ZigBee, and Ericson Bluetooth specifications for short range radio technology, or an Infrared Data Association (IrDA) light wave technique.

The present design provides a system and method for bonding a Bluetooth master device to a Bluetooth slave device. The method includes a novel wired arrangement for use during the searching phase that may enable a Bluetooth master device to obtain a single Bluetooth slave device unique address without using an over-the-air technique. Furthermore, once the unique slave device address is obtained, the wire is disconnected and the Bluetooth pairing phase begins. The Bluetooth pairing phase is accomplished by switching over to a wireless communications network between the Bluetooth master and slave device.

The operation of today's current state of design for Bluetooth connection establishment will be described in the paragraphs that follow. The teachings are intended to provide a basic foundation for Bluetooth bonding using over-the-air techniques. This basic foundation will form the framework for describing the present design system and method.

In order to establish a connection between a master and slave device in a Bluetooth compliant system, the master device initiates a device bonding process. The bonding process consists of a searching phase and a pairing phase. The searching phase, initiated by the Bluetooth master device, is used to discover all available Bluetooth slave devices. During the searching phase, each slave device responds with its unique address. The Bluetooth master device reports and stores the received addresses. If the intended slave device is not found, the searching process is repeated. After the searching phase concludes, the Bluetooth master device initiates the pairing phase. The pairing phase is used to provide an authentication mechanism between the master and slave device. Successful completion of the pairing phase results in a communication path being established between these two Bluetooth enabled devices.

The bonding process is suitable in a variety of applications and environments. For example, a cellular phone handset may act as a Bluetooth master device and initiate the bonding process with an integrated earpiece and microphone Bluetooth slave device to establish a wireless communication path enabling bi-directional transfer of data and information. In this environment, the searching phase can be achieved in a very short amount of time since there are a limited number of devices available for the cellular phone handset to search.

FIG. 1A illustrates an exemplary communication system 100 employing Bluetooth technology to provide a communications path across wireless communications network 130 between antenna 114 connected to controller 110 and antenna 115 connected to wireless device 111. For purposes of illustration, an instrument host 120 manages the wireless controller 110, and the wireless device 111 provides a footpedal 121 used in controlling the instrument host 120. The communication system 100 facilitates bi-directional communication between the instrument host 120 and footpedal 121. The Bluetooth technology is realized by employing a Bluetooth master device 112 and a Bluetooth slave device 113, wherein the Bluetooth master device 112 and the Bluetooth slave device 113 access the wireless communications network 130 to form a communications path between antennas 114 and 115 respectively.

Bluetooth employs a bonding process to establish a new relationship between two Bluetooth enabled devices before they can exchange data. In this context, bonding refers to a mechanism where the two devices are exchanging protected passkeys and form a link. Once bonded, all data and information transmitted over this Bluetooth link is encrypted and only those slave devices authorized during the bonding process will be able to receive and decipher this encrypted transmission.

In order to establish a connection between a master and slave device in a Bluetooth compliant system, the master device initiates a device bonding process. The master device first searches for one or more slave devices, and second pairs with the slave devices to accomplish the bonding process.

First, the Bluetooth address of each slave device must be registered with its corresponding Bluetooth master. This may be accomplished by an instrument host 120 system sending commands to the controller 110 to request the Bluetooth master device 112 to acquire over fixed cable 140 the slave device address. Once the master device 112 acquires the slave device Bluetooth address, it will only pair with the slave device having this address.

Figure 1B:
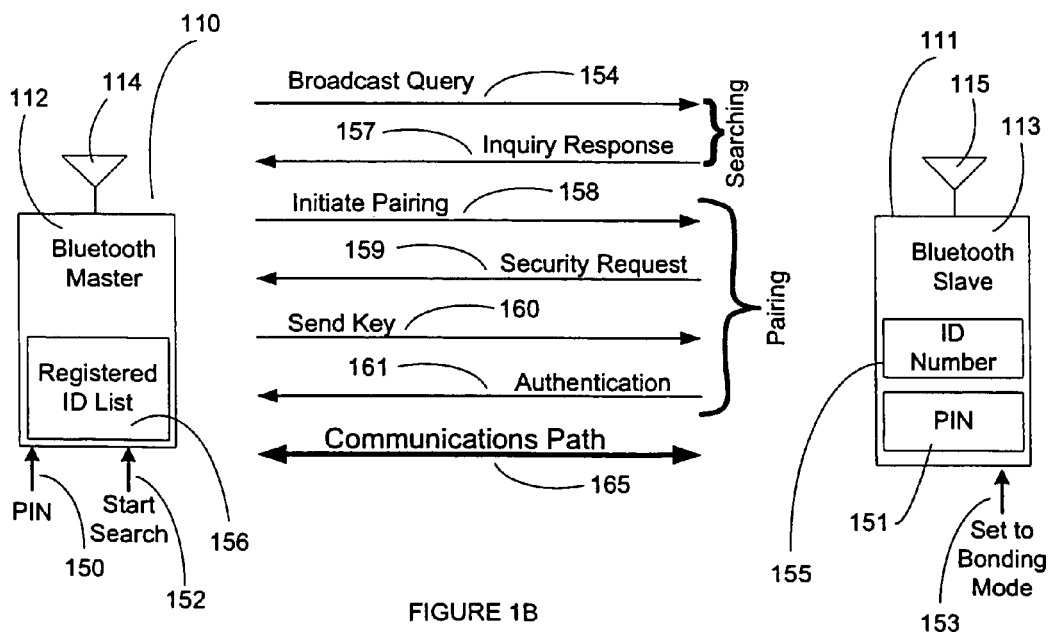
FIG. 1B illustrates the Bluetooth bonding mechanism components, interfaces and sequence of events for searching and pairing a master and slave Bluetooth enabled devices.

FIG. 1B illustrates the Bluetooth bonding mechanism between the Bluetooth master device 112 and the Bluetooth slave device 113. Before the bonding process can begin, a PIN code must be entered into both Bluetooth devices. Note that in some slave devices, for example wireless earphones, footpedal switches, and other peripheral devices, the PIN is fixed and cannot be changed. In such cases, the fixed PIN is entered into the Bluetooth master device 112. To start the bonding process, the Bluetooth slave device 113 must be set in the bonding mode. This is typically achieved by pressing a button on the wireless device 111 at 153. Bonding mode enables the Bluetooth slave device 113 to listen on antenna 115 for inquiry requests originating from the Bluetooth master device 112 as it transmits inquiry request on antenna 114 across the wireless communications network 130. Next, the fixed PIN 151 value stored within the Bluetooth slave device 113 is entered into controller 110. This is typically accomplished by the user entering the PIN 151 manually into the Bluetooth master device 112 at 150, or may be supplied electronically by an external system in the form of automatic provisioning at 150 (not shown).

At this point, the user may instruct the Bluetooth master device 112 to begin transmitting multiple inquiry requests to search for all available and in range Bluetooth slave devices 113. Typically the user selects begin search mode by selecting from a menu at 152 (not shown). Beginning search mode causes a broadcast query 154 to be sent from the Bluetooth master device 112 to in range Bluetooth slave devices 113 for the purposes of discovering their Bluetooth addresses. Each Bluetooth slave device 113 that receives the broadcast query 154 follows a response procedure to return an inquiry response 157 to the Bluetooth master device 112. This response procedure includes the slave device providing its unique identification number 155 (i.e. address). The slave device may encapsulate its address in its inquiry response message. In parallel, the Bluetooth master device 112 listens for all inquiry responses 157 generated by the in range Bluetooth slave devices 113. The Bluetooth searching phase basically allows the master device to discover all available in range slave devices. The Bluetooth master device 112 compares each returned unique address to the Bluetooth slave addresses initially registered with and stored in the Bluetooth master device 112 at 156. When the Bluetooth master device 112 matches an address retuned from a slave device 113 to a registered identifier number, the searching phase is completed.

Next, the Bluetooth master device initiates pairing 158 with the registered slave device possessing the matching address. The slave device responds to the initiate pairing 158 request by sending a security request 159 as part of the pairing process. The Bluetooth master device 112 responds to the security request 159 by generating a key generated from the previously entered PIN number and sends this key at 160 to wireless device 111. If the Bluetooth master device 112 sends a valid key based on having the correct PIN number for the intended slave device, the Bluetooth slave device 113 will return an authentication 161 message. On successful authentication, the Bluetooth master and slave device form a communications path 165 and invokes encryption across this link based on the supplied key. Thus the pairing phase of the bonding process completes and the two devices are now able to send and receive data and information across this path.

Figure 1C:
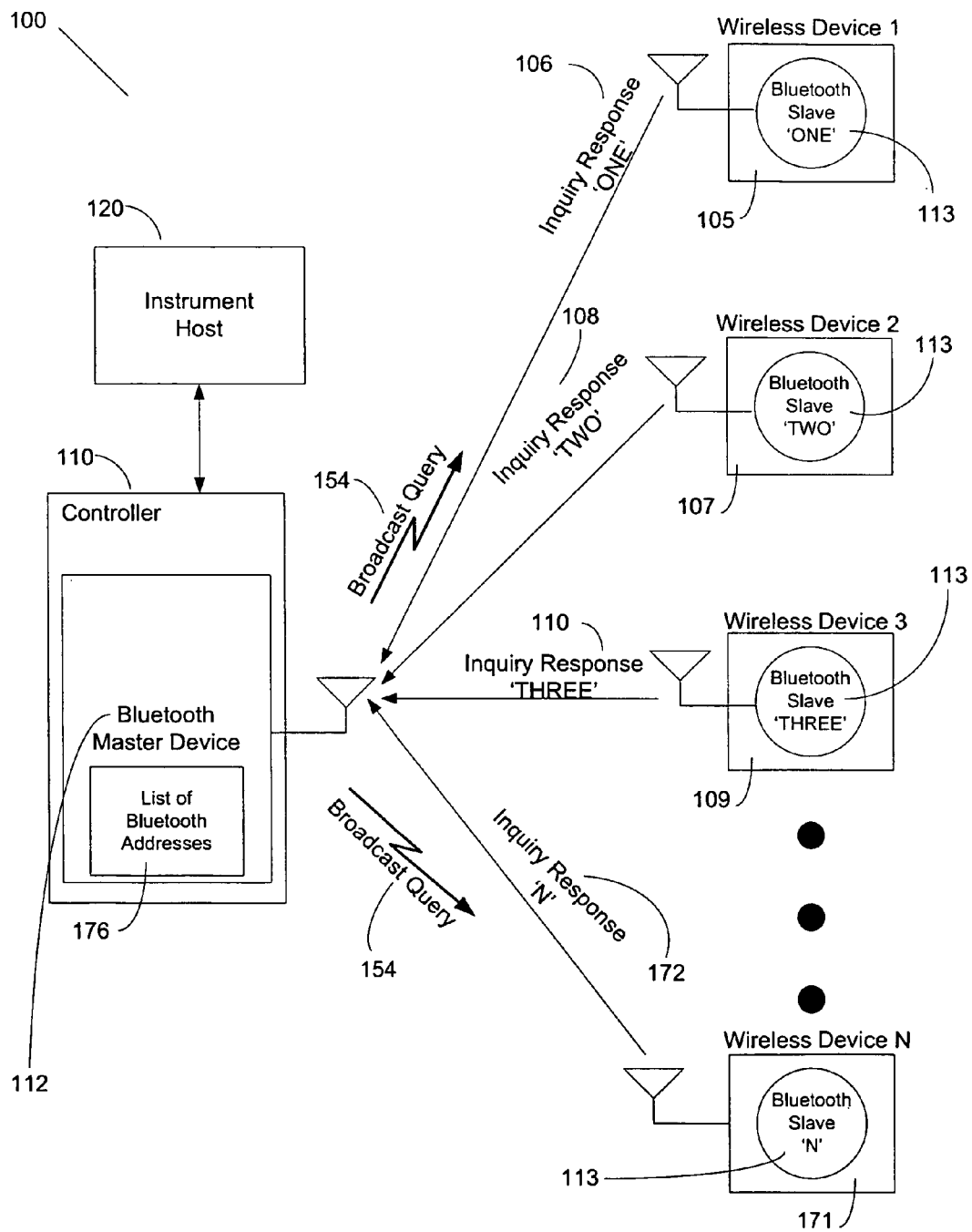
FIG. 1C illustrates the Bluetooth bonding mechanism in an environment where a plurality of Bluetooth slave devices are present and within broadcast query range.

FIG. 1C illustrates an exemplary wireless communication system 100 employing a plurality of Bluetooth slave devices 113 and one Bluetooth master device 112. The Bluetooth master device 112 begins a device bonding process by sending a broadcast query 154 to all Bluetooth slave devices 113.

The transmission of the broadcast query 154 from the Bluetooth master device 112 initiates a search for all Bluetooth slave devices 113 that are within reception range. The broadcast query 154 requests each Bluetooth slave device 113 to return its unique Bluetooth address 155.

For example, wireless device one at 105 replies to the broadcast query 154 by sending an inquiry response 157 and provides its unique address 'ONE' at 106 to Bluetooth master device 112. Wireless device two at 107 replies to broadcast query 154 by sending an inquiry response 157 and provides its unique Bluetooth address 'TWO' at 108. Wireless device three at 109 replies to the broadcast query 154 by sending an inquiry response 157 and provides its unique Bluetooth address 'THREE' at 110. And, in this example, all in reception range wireless devices reply to the Bluetooth master device 112 broadcast requests 154. Wireless device 'N' at 171 replies to the broadcast query 154 by sending an inquiry response 157 and provides its unique Bluetooth address 'N' at 172. Bluetooth master device 112 creates and maintains a list of Bluetooth addresses at 176 received from the queried wireless devices 105, 107, 109 and 171. The Bluetooth master device 112 compares the returned Bluetooth addresses to the address originally sent by the instrument host 120 or provided by the user. In this example, the instrument host 120 provided the Bluetooth master device 112 the unique address 'ONE' (not shown). The Bluetooth master device 112 searches the list of Bluetooth addresses 176 for a slave device that matches the previously registered unique address list stored at 156. In this example, the Bluetooth master device 112 matches with wireless device one at 105 since it returned the desired unique address 'ONE'.

Bluetooth master device 112 then initiates a pairing process with wireless device 105. This is accomplished by the Bluetooth master device 112 connecting and communicating with only the Bluetooth slave device reporting the desired registered address and thus completes the pairing process. Once the pairing process concludes successfully, a wireless communications path 165 is established and becomes available for use between controller 110 implementing Bluetooth™ master device 112 and the intended wireless device one 105 implementing Bluetooth™ slave device 113 functionality.

Figure 2:
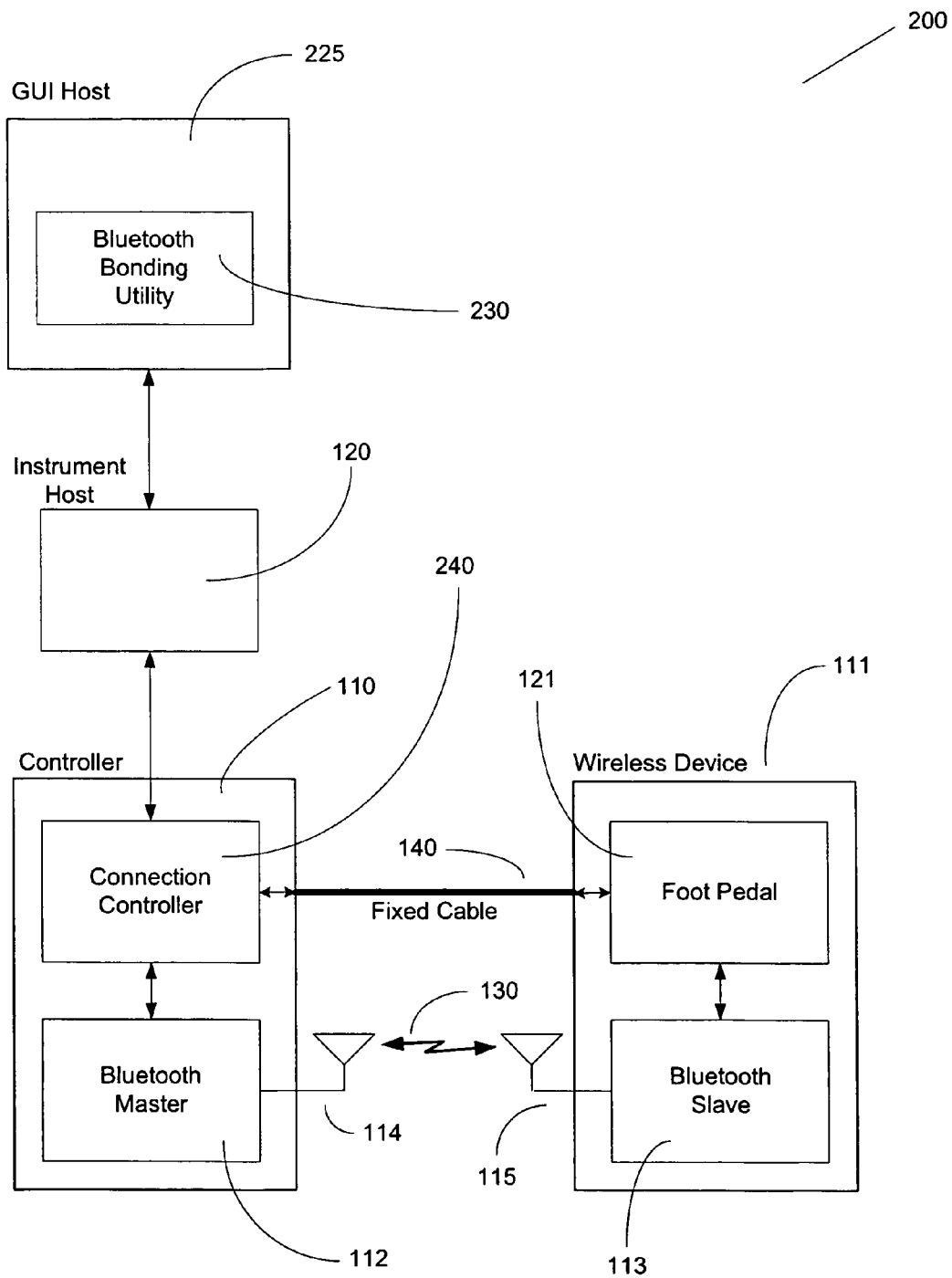
FIG. 2 illustrates the present design components and interfaces for a wireless medical system 200, where the particular embodiment contemplates that the wireless or remote device is a footpedal switch.

FIG. 2 illustrates the present design components and interfaces for a wireless medical system 200, where the particular embodiment illustrated in FIG. 2 contemplates that the wireless or remote device is a footpedal 121 switch. The medical system 200 in this embodiment includes a wireless device 111, a controller 110, an instrument host system 120, and a wireless communications network 130. In addition, a graphical user interface (GUI) host 225 with an embedded Bluetooth bonding utility 230 may be connected to the instrument host in order to facilitate automation of the present design method. A footpedal 121 may transmit control signals relating internal physical switch position information, not shown in this view, as input to the wireless device 111. The footpedal 121 may provide data indicating physical and virtual switch position information to a Bluetooth slave device 113. The Bluetooth™ slave device 113, typically comprising a transmitter and receiver operating, for example, using the wireless or Bluetooth protocols, may transmit this data using a wireless communication network 130 via antenna 115.

One approach to digital electronic footpedal control system, especially for a medical device, is described in U.S. Pat. No. 4,983,901, entitled "Digital Electronic Foot Control for Medical Apparatus and the Like", issued Jan. 8, 1991, the entirety of which is incorporated herein by reference. A typical footpedal design is further provided in U.S. Pat. No. 5,268,624, entitled "Footpedal Control with User-selectable Operational Ranges" issued Dec. 7, 1993, the entirety of which is incorporated herein by reference.

The wireless communications network 130 may employ any network communications protocol sufficient for serving the purposes of communications network 130. Additionally, the term "communications network" or "communications system" as used herein is used in its most expansive sense and applies to any communications system through which any information may be transferred to and from a wireless device, and includes, without limitation, transmission by static, active, dynamic communications protocols or otherwise. While the present design may use various communication protocols, it will be discussed herein implementing and complying with Ericsson's Bluetooth protocol specification. Slight changes may be made to the enclosed to enable operation using other or complementary communications protocols, and the use and implementation of the present design using these other protocols is intended to be within the scope of the current design.

From wireless communication network 130 via antenna 114, the controller 110 receives wireless device 111 transmissions via a Bluetooth master device 112. The Bluetooth master device 112 receives and forwards data, including but not limited to information such as footpedal position and state parameters, to the connection controller 240. The connection controller may in turn forward footpedal 121 position and state parameters to instrument host 120. Position and state information, may include but is not limited to representing relative pitch and yaw travel of the footpedal 121, as well as buttons, switches, or other input devices on footpedal 121. Moreover, the controller 110 may provide redundant wireless connections supporting a primary communication path, and one or more backup communication paths to ensure reliable exchange of data (not shown).

The instrument host 120 may use the received data to control and operate the behavior of various embedded features and functions including irrigation, aspiration, electrical cauterization, and various cutting actions, such as phacoemulsification and vitrectomy procedures, and providing pressure for posterior ocular segment surgery, such as viscous fluid injection. The instrument host 120 may use the data to effectuate a switch between hand-pieces, modes, or modules, such as switching between a phacoemulsification procedure and a vitreous cutting procedure. Such a switch may be effectuated by the operator providing an indication on a switch or button on footpedal 121 that indicates a desired switch between procedures or modules.

In a similar manner, the instrument host 120 may provide information to the controller 110, including but not limited to information such as control signals indicating the amplitude and duration to command the footpedal 121 vibration device, such as a vibration motor or solenoid actuator (not shown), sufficient to provide tactile feedback to the surgeon. In addition, the instrument host 120 may provide information to the controller 110 for the purposes of providing cues, such as activating status lights and emitting sounds, on the footpedal to alert the operator. The controller 110 may forward information received from the instrumentation host 120 to the wireless device 111. The Bluetooth master device 112 in controller 110 may transmit this information across the wireless communications network 130 to the wireless device 111 Bluetooth slave device 113. The Bluetooth slave device 113 may deliver the control signal information to the footpedal 121; thus resulting in the operation of the vibration motor or other feedback mechanisms within the footpedal 121 in accordance with the supplied control signal amplitude and duration.

Furthermore, the controller 110 and the wireless device 111 may monitor the health and status of the primary and backup Bluetooth data channels, including but not limited to data channel signal quality and strength.

While depicted as multiple elements, connection controller 240 and Bluetooth master device 113 may alternatively be comprised of a single firmware device or a set of distributed firmware devices that fulfill the functionality of connection controller 240 and Bluetooth master device 113. Additionally, while depicted as multiple elements, footpedal 121 and Bluetooth slave device 113 may also be comprised of a single firmware device or a set of distributed firmware devices that fulfill the functionality of footpedal 121 and Bluetooth slave device 113.

In general, the present design includes a system and method for bonding a Bluetooth master device with one or more Bluetooth slave devices, including but not limited to discovering one or more Bluetooth slave devices and authenticating with each slave device to form a communications path between a master and a slave device. The novel arrangement and method of the present design enables the slave address of the intended device to be obtained using a wire mode for connecting the slave device to the controller 110, thus bypassing the Bluetooth wireless searching mechanism depicted in FIG. 1C. Once the system obtains and stores the address, the system removes the wired connection and the wireless mode is used to performing the pairing phase over the wireless communications network 130. The present design system and method ensures or guarantees that the address of the intended device is always found accurately.

Generally, the present design introduces a new discovery arrangement that replaces the Bluetooth™ master device wireless broadcast query, offered with previous systems, with a query response method across a physically connected or wired cabled between the controller 110 and the wireless device 111 implementing Bluetooth slave device functionality.

Figure 3:
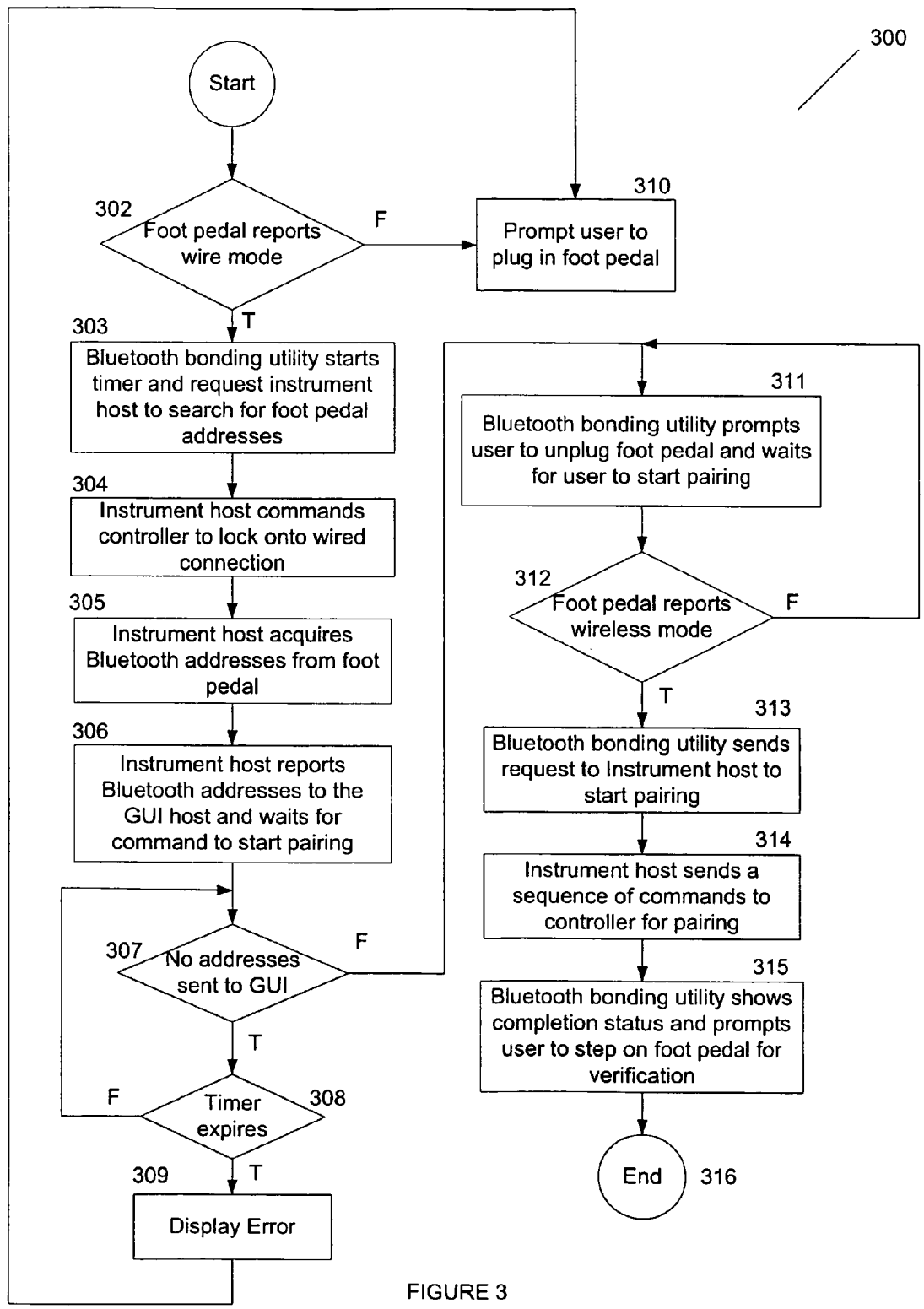
FIG. 3 is a flowchart representing the implementation and operation of the present design.

FIG. 3 illustrates general operation of the system. From FIG. 3, point 302 establishes whether a footpedal is connected in the wired mode. If the footpedal is not physically connected, the user is prompted to plug in the footpedal at point 310. When the present design reports the footpedal is in wired mode at point 302, the Bluetooth bonding utility may start a timer and request the instrument host to discover the footpedal address over the fixed cable 130. The present designs discovery method may send commands from the instrument host 120 at point 304 to the controller 110 instructing the connection controller 240 to lock onto the wired connection.

The instrument host 120 acquires the Bluetooth address from the footpedal at 305. The instrument host may report the Bluetooth address obtained from wireless device 111 to the GUI host 225 at point 306. The instrument host 120 is now ready to begin the authentication or pairing process. Authentication is preferably conducted over the wireless communications network 130; however, authentication may also be conducted over the fixed cable 140 or any other wired or wireless device or system suited for this task. In the situation where no slave device 113 addresses are reported at point 307 to the GUI host 225, a timer may expire at point 308 and an error may be displayed to the user at point 309. If the timer has not expired, the GUI host 225 continues to listen for slave device 113 addresses to be reported by the instrument host 120. If the instrument host 120 sends addresses to the GUI host 225, the Bluetooth bonding utility may prompt the user to unplug the fixed cable 140.

At point 312, the footpedal 121 reports being configured and operating in wireless mode. The Bluetooth bonding utility may send a request to the instrument host 120 to begin pairing at point 313. The instrument host 120 may send a sequence of commands to controller 110 for authentication and pairing at point 314. Once the controller 110 and wireless device 111 successfully bond, the controller 110 reports to the instrument host 120 that the communication path 465 between the two devices has been established. At point 315, the Bluetooth bonding utility 230 may show a completion status to the user and may prompt the user to step on the footpedal 121 to verify operation. When the communications path 465 is verified, the process ends at point 316 and the devices are now ready for use.

Figure 4A:
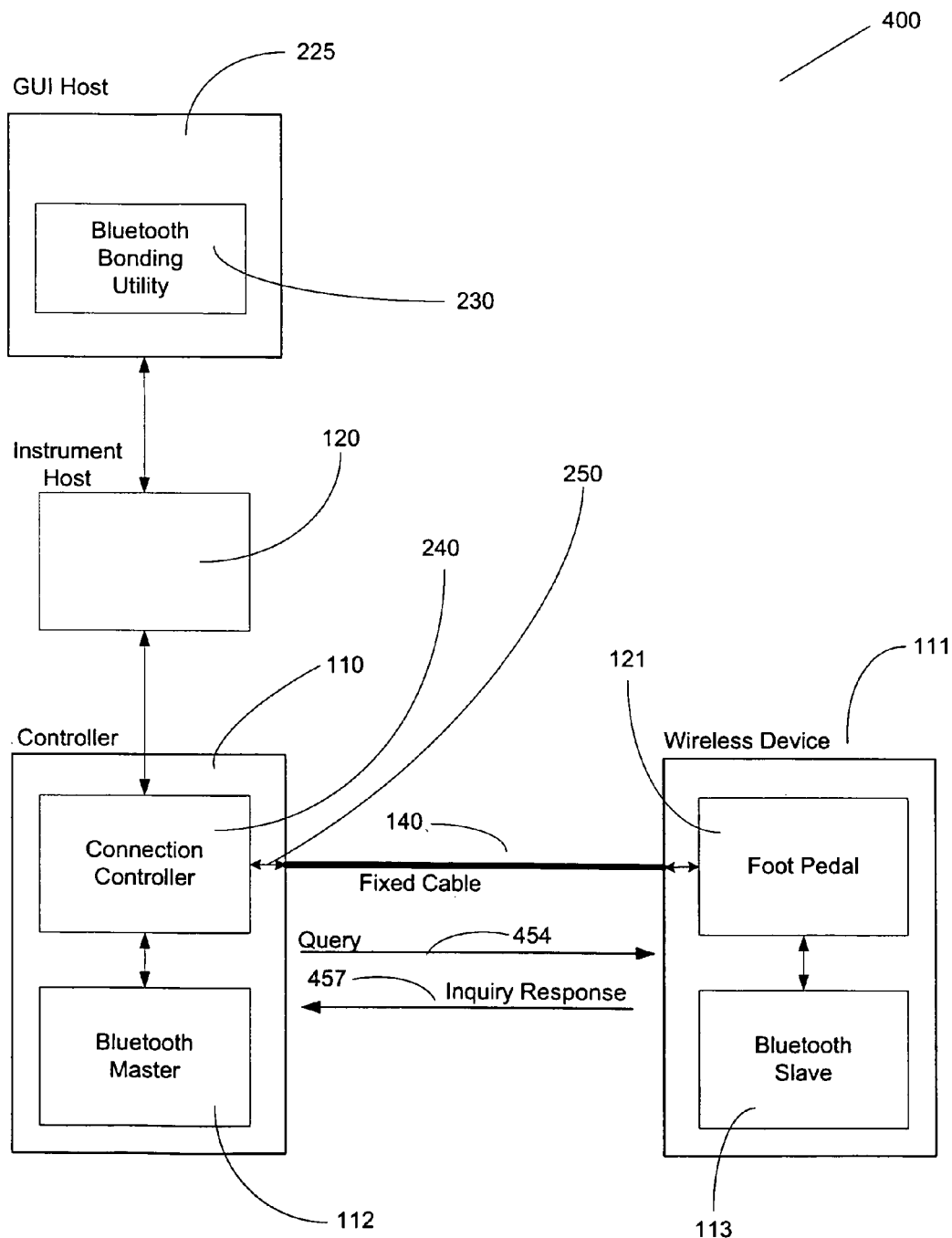
FIG. 4A illustrates the present design components and interfaces for a wireless medical system 400, where the particular embodiment contemplates that the medical system is configured for searching and discovering a wireless device Bluetooth address over fixed cable.

The present design will now be described in relation to a general medical system 400. The particular embodiment illustrated in FIG. 4A contemplates that the medical system is configured in an arrangement that may allow controller 110 to provide a mechanism suitable for searching and discovering a wireless device 111 Bluetooth address or other information stored in a wireless device 111 using a fixed cable 140.

During the surgical day, after the user powers on the instrument host 120, the user may launch the Bluetooth bonding utility 230 to pair the system with a new footpedal or to re-establish the pairing with the footpedal in when the system self-test fails to detect the footpedal. The Bluetooth bonding utility 230 may present to the user a graphical user interface for controlling the Bluetooth connection establishment and activation process. Initially, the Bluetooth bonding utility 230 may report that no footpedal is present in wired mode, indicating that the apparatus is not properly configured. If no footpedal is present, the Bluetooth bonding utility 230 may prompt the user to locate the desired footpedal and associated fixed cable 140 and instruct the user to connect the footpedal 121 to controller 110 using the fixed cable 140 wire. When the physical cable is attached, the connection controller 240 may electronically detect the fixed cable 140 wire is presence at port 250 and may signal the instrument host 120 indicating that the cable is in place, functioning, and ready for use. The instrument host 120 may relay this connection state information to the Bluetooth™ bonding utility 230 indicating that the footpedal is ready for starting the connection establishment and discovery process with wireless device 111 across this fixed cable 140. In addition, the present design Bluetooth address discovery method may instruct the connection controller 240 to disable the resident Bluetooth master device 112 functionality in order to prevent the master device 112 from transmitting one or more broadcast queries 154 over wireless network 130.

At this point, the Bluetooth bonding utility 230 may initiate a connection establishment and activation process and may send a request to the instrument host 120 to begin searching for the desired footpedal 121 device address. The instrument host 120 may send commands to instruct the controller 110 to lock onto the wired connection. When locked, the instrument host 120 acquires the Bluetooth address from the footpedal 121. The connection controller 240 may then send a query 454 to footpedal 121 requesting its stored Bluetooth address. The Bluetooth slave device 113 may respond to this query by reporting its address by embedded its address in an inquiry response 457. The controller 110 may extract this address from the inquiry response 457 and may forward this address to the instrument host 120, which then in turn may forward, or report, the unique address to the Bluetooth bonding utility 230. On receipt of this address, the Bluetooth bonding utility 230 may recognize that the discovery phase of the bonding process successfully completed. The Bluetooth bonding utility 230 may prompt the user to disconnect the fixed cable 140, thus preparing the controller 110 and wireless device 111 to begin wireless operation and begin the present designs authentication process.

Figure 4B:
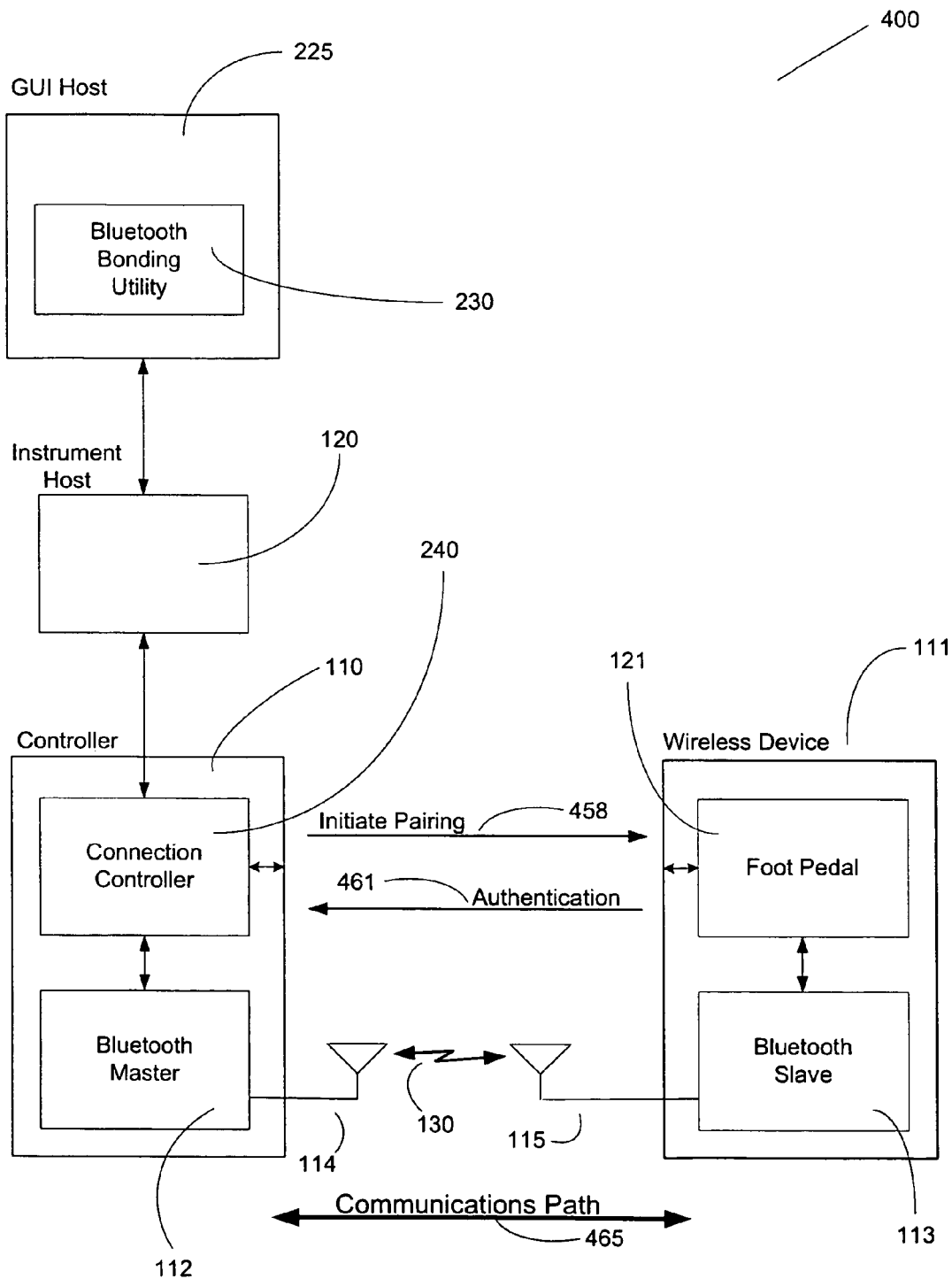
FIG. 4B illustrates the present design components and interfaces for a wireless medical system 400, where the particular embodiment contemplates that the apparatus is configured in a wireless arrangement, ready to conduct the authentication process.

The particular embodiment illustrated in FIG. 4B contemplates that the medical system 400 is configured in an arrangement that may allow controller 110 to provide a mechanism suitable for pairing and authenticating with wireless device 111 Bluetooth across wireless communications network 130.

The controller 110 may send a signal to the instrument host 120 indicating the fixed cable is no longer present and is now switched to operating in the wireless mode. The instrument host 120 may forward this signal to the Bluetooth bonding utility 230. At this point, the user may instruct the Bluetooth bonding utility 230 to initiate the authentication or pairing process. The Bluetooth bonding utility 230 may send a request to the instrument host 120 to start authentication. The instrument host 120 may send a sequence of commands to the controller 110 for pairing. The Bluetooth master device 112 may respond to the sequence of commands sent from instrument host 120 by first sending an initiate pairing 458 request to the Bluetooth slave device 113 having the address previously discovered and stored in list of Bluetooth addresses 176 over wireless communications network 130. The Bluetooth master device 112 may attempt to pair with only the wireless device that previously reported its unique address during the wired discovery process. When the intended Bluetooth slave device 113 within wireless device 111 receives an initiate pairing request 458, the intended slave device may reply with an authentication 461 message indicating that the authentication process was successful.

At this point, the master and slave devices may form a communications path 465 over wireless network 130 for exchange of data and information. The controller 110 may forward a completion status to instrument host 120 destine for the Bluetooth bonding utility 230. The Bluetooth bonding utility 230 may prompt the user to step on footpedal 121 to verify the wireless operation of footpedal 121 across communications path 465.

The controller 110 then bonds with the wireless device 111 to enable communication of control signal and other device information, such as battery condition. The specific techniques and details associated with Bluetooth searching and pairing mechanism is generally known to those skilled in the art.

In the situation where the Bluetooth master device 112 does not receive the desired Bluetooth address from a slave device within a predetermined amount of time, the process may time-out and the controller 110 may return a failed to locate message to the instrument host 120, which in turn may provide this information to the Bluetooth bonding utility 230 indicating the desired slave device was not found within range. The Bluetooth bonding utility may then report this status to the end user and may prompt the user to select from a number of choices, including re-attempt connection with same slave device, enter a different slave device for connection establishment, and quit search.

The present design may ensure that only a one-to-one relationship is formed between the Bluetooth master device 112 and a single Bluetooth slave device 113 by using the fixed cable 140 to obtain the address of the slave device. By preserving this one-to-one relationship, this method ensures safe operation within one or more operating theaters by only being capable of bonding with the Bluetooth slave device 113 named in the list of Bluetooth addresses 176. In addition, the present designs may enable a quick and reliable method for connecting a footpedal 121 prior to the start of a surgical procedure, where numerous footpedals may be stored. Furthermore, if a footpedal 121 becomes inoperable during a surgical procedure, the present designs may enable a quick and reliable method for exchanging a footpedal 121 during a surgical procedure, and to connect the footpedal when instrument host 120 equipment is moved from one operating theater to a different theater.

Moreover, in a mass production environment, the present designs method of obtaining the address over a fixed cable 140 eliminates the wireless searching phase associated with Bluetooth discovery, which as previously stated, may fail to find the intended device.

Furthermore, the present designs method may allow a user to pre-populating the list of Bluetooth addresses 176 with up to seven desired unique addresses. Pre-populating is accomplished via the Bluetooth bonding utility 230. This method may significantly reduce the total amount of time required for wireless pairing of a Bluetooth master and a slave device to form a communications path 465. This efficiency may significantly reduce the total time required for quality control and other tests required in a mass production environment while improving accuracy.

Figure 5:
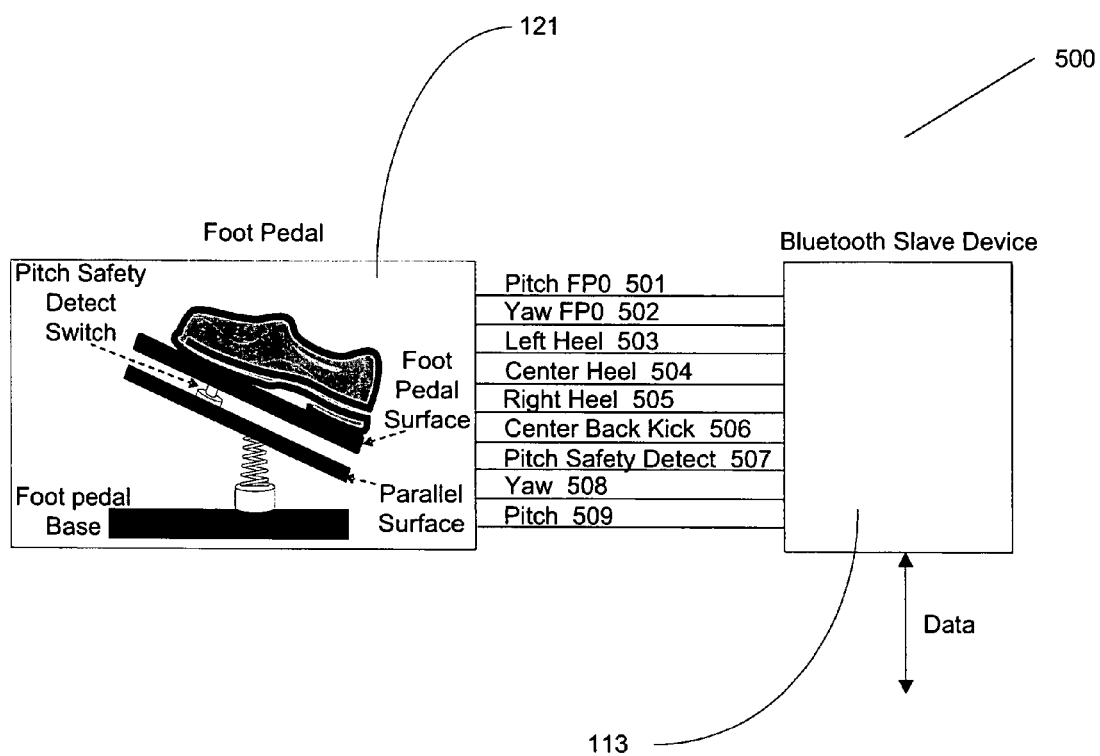
FIG. 5 illustrates a footpedal that may be employed in accordance with the current design.

FIG. 5 illustrates a footpedal 121 that may be employed in accordance with the current design. In the embodiment illustrated, the Bluetooth slave device 113 receives one or more control signals from the footpedal 121. The control signals generated by the footpedal 121 may report the status of various physical and virtual switches contained within or other parameters such as yaw linear position and vertical linear position. The footpedal firmware within the footpedal 121 reads and processes the switch inputs. The footpedal 121 produces a data stream representing control signals resulting from the button and switch positions triggered on the footpedal 121. The control signals are ultimately destined for the instrument host 120. Control signals may include but are not limited to position of a footpedal, such as left heel 503, center heel 504, right heel 505, pitch safety detect 506, pitch 507, and yaw 508 positions; button pushes or "stomp" values, or other appropriate states in the case of a footpedal. Moreover, predefined footpedal positions FP0, FP1, FP2, or FP3 (FPn) may be communicated. For example, pitch FP0 501 and yaw FP0 502 may be communicated when the foot 121 connected.

Figure 6:
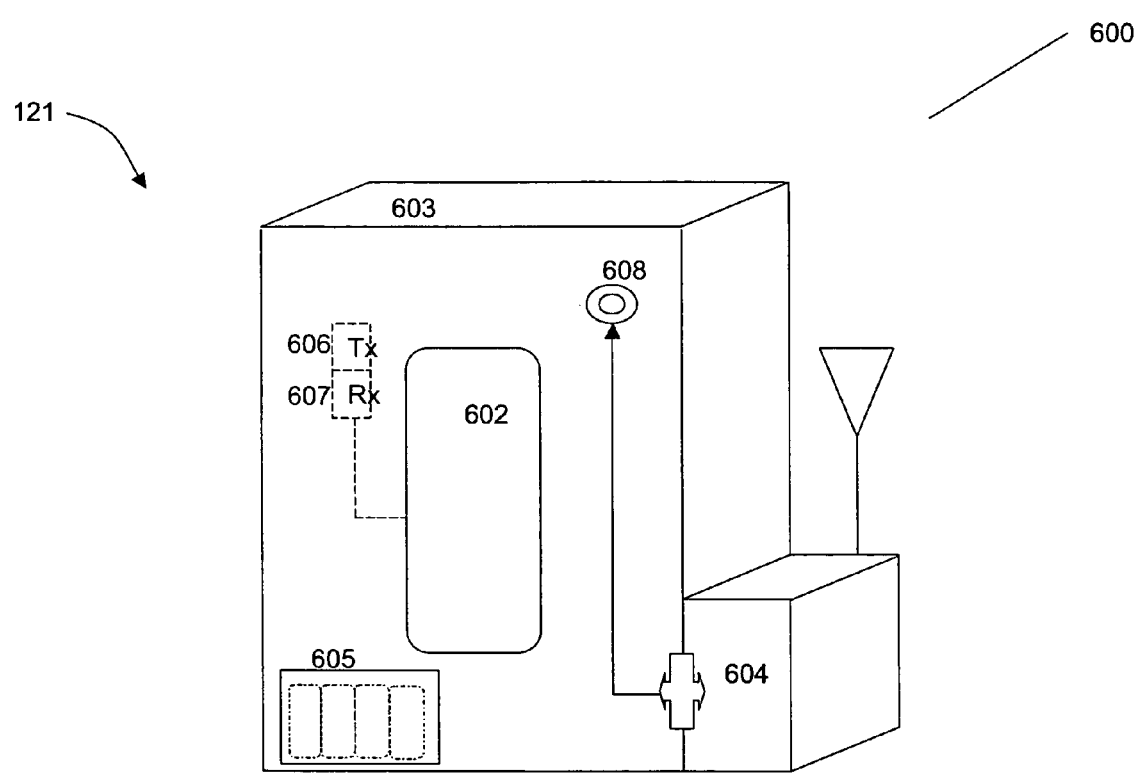
FIG. 6 shows the conceptual connections between the footpedal and the base unit and power source.

FIG. 6 shows the conceptual connections between the footpedal 121 and the base unit and power source. Footpedal 1121 includes pedal 602, base 603, and communications interface 604 here shown at the side of the base 603. The footpedal 121 in this view includes batteries 605, typically rechargeable batteries. A transmitter 606 and receiver 607 are provided in the footpedal 121 in this embodiment and connect to the communications interface 604 to access the antenna 115, and in this embodiment a "connection LED" 608 is provided that is constantly on when the both wireless device 111 data channel is available for operational use. When a data channel becomes disconnected due to interference or other causes, the connection LED 608 may blink on and off, warning the user that one data channel is lost or disconnected and communication redundancy is not available. Blinking in this manner enables the surgeon to decide whether to continue the procedure or wait until the lost data channel is restored. Other notification methods may be employed, including but not limited to optical (e.g. one LED per channel) and audio notification methods.

The foregoing is not determinative or exclusive or inclusive of all components, interfaces, communications, and operational modes employable within the present design. The design presented herein and the specific aspects illustrated are meant not to be limiting, but may include alternate components while still incorporating the teachings and benefits of the invention, namely a wireless device communication management apparatus employing a wireless medical device, wireless controller, a communications network, and instrument host system to facilitate surgeons while performing procedures. While the invention has thus been described in connection with specific embodiments thereof, it will be understood that the invention is capable of further modifications. This application is intended to cover any variations, uses or adaptations of the invention following, in general, the principles of the invention, and including such departures from the present disclosure as come within known and customary practice within the art to which the invention pertains.

What is claimed is:

1. A method for establishing a wireless connection between an instrument host and at least one non-fixed medical device, comprising:
    providing a fixed cable wire connection between the instrument host and the non-fixed medical device, wherein the instrument host is a component of a phacoemulsification system, wherein the non-fixed medical device comprises a footpedal switch for use with the instrument host, and wherein the instrument host provides master device functionality and the non-fixed medical device provides slave device functionality;
    discovering a slave device address of the non-fixed medical device over said fixed cable wire;
    authenticating the non-fixed medical device; and
    removing the fixed cable wire between the instrument host and the non-fixed medical device before authenticating the instrument host with the non-fixed medical devices, wherein the authenticating is performed over a wireless communications network.

2. The method of claim 1, further comprising managing the discovering and authenticating using a Bluetooth bonding utility.

3. The method of claim 2, wherein the providing further comprises:
    reporting the absence of the fixed cable wire to the user via the Bluetooth bonding utility from a connection controller;
    instructing the user, via the Bluetooth bonding utility, to attach the fixed cable wire when the fixed cable wire is reported as not present;
    detecting the presence of the fixed cable wire by the connection controller; and
    reporting the presence of the fixed cable wire to the user via the Bluetooth bonding utility from the connection controller.

4. The method of claim 1, further comprising storing the slave device address of the non-fixed medical device obtained over the fixed cable and making said address available to the slave device master device for use during authentication.

5. The method of claim 1, wherein discovering further comprises:
    sending a query message over the fixed cable wire from the master device to the slave device requesting the slave device address;
    replying to said query message by sending an inquiry response message over the fixed cable wire from the slave device to the master device wherein the slave device address is encapsulated in the inquiry response.

6. The method of claim 1, further comprising managing the discovering and authenticating using a Bluetooth bonding utility, and wherein removing the fixed cable wire further comprises:
    instructing the user to disconnect the fixed cable wire when the Bluetooth bonding utility obtains the slave device address from the controller;
    detecting the fixed cable wire is removed from the controller to the Bluetooth bonding utility; and
    indicating to the user that the non-fixed medical device and instrument host are ready and available for authentication via the Bluetooth bonding utility.

7. The method of claim 1, wherein the wireless connection is a Bluetooth wireless connection.

8. A method for establishing a wireless connection between an instrument host and at least one non-fixed medical device, comprising:
    providing a fixed cable wire connection between the instrument host and the non-fixed medical device, wherein the instrument host is a component of a phacoemulsification system, wherein the non-fixed medical device comprises a footpedal switch for use with the instrument host, and wherein the instrument host provides master device functionality and the non-fixed medical device provides slave device functionality;
    discovering a slave device address of the non-fixed medical device over said fixed cable wire;
    authenticating the non-fixed medical device;
    removing the fixed cable wire between the instrument host and the non-fixed medical device before authenticating the instrument host with the non-fixed medical device, wherein the authenticating is performed over a wireless communications network; and
    locking the fixed cable wire connection to prevent the non-fixed medical device from switching into a wired mode.

9. A connectivity management system, comprising:
    an instrument host, comprising:
    a bonding utility; and
    a controller configured to control communications with at least one obtained slave device over a fixed wire;
    a non-fixed medical device configured to support wired and wireless modes of operation, wherein the non-fixed medical device comprises a footpedal switch;
    a fixed wire connecting the instrument host to the non-fixed medical device; and
    a wireless communications network;
    wherein the instrument host is a component of a phacoemulsification system and wherein the instrument host is configured to discover a slave device address of the non-fixed medical device over said fixed wire and authenticate the non-fixed medical device after removing the fixed wire between the instrument host and the non-fixed medical device, wherein the authentication is performed over a wireless communications network.

10. The system of claim 9, wherein the bonding utility comprises a graphical user interface for managing discovery and authentication.

11. The system of claim 9, wherein the instrument host controls and operates selected functionality of the non-fixed medical device.

12. The system of claim 9, wherein the controller comprises Bluetooth master device functionality capable of transmitting information to and receiving information from the non-fixed medical device.

13. The system of claim 9, wherein the non-fixed medical device comprises Bluetooth slave device functionality capable of transmitting information to and receiving information from the controller.

14. The system of claim 9, wherein the bonding utility is a Bluetooth bonding utility.

15. A method for providing Bluetooth communications between a non-fixed medical device and a controller, comprising:

acquiring a Bluetooth address of the non-fixed medical device over a fixed cable wire;

registering said non-fixed medical device Bluetooth address in a list of Bluetooth addresses maintained by said controller; and authenticating said non-fixed medical device with said controller over a wireless communications network after removing the fixed cable wire between the controller and the non-fixed medical device, wherein the controller is a component of a phacoemulsification system and wherein the non-fixed medical device comprises a footpedal switch.

16. The method of claim 15, wherein acquiring further comprises sending the Bluetooth address of the non-fixed medical device in response to queries from the controller.

17. The method of claim 15, wherein registering further comprises storing the non-fixed medical device Bluetooth address received over the fixed cable wire within the controller.

* * * * *

UNITED STATES PATENT AND TRADEMARK OFFICE
CERTIFICATE OF CORRECTION

PATENT NO. : 7,636,549 B2
APPLICATION NO. : 11/408763
DATED : December 22, 2009
INVENTOR(S) : Ma et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 802 days.

Signed and Sealed this

Ninth Day of November, 2010

David J. Kappos
*Director of the United States Patent and Trademark Office*